United States Patent [19]

Peterson et al.

[11] 4,011,501
[45] Mar. 8, 1977

[54] APPARATUS AND METHOD FOR DETERMINING MOISTURE CONTENT IN WELDING ELECTRODE COATINGS

[75] Inventors: Marvin L. Peterson; Charles F. Cole, Jr., both of Ponca City, Okla.

[73] Assignee: Continental Oil Company, Ponca City, Okla.

[22] Filed: Nov. 21, 1975

[21] Appl. No.: 634,093

[52] U.S. Cl. .............................................. 324/65 R
[51] Int. Cl.² ........................................ G01R 27/02
[58] Field of Search ....................... 324/65 R, 65 P

[56] References Cited
UNITED STATES PATENTS

| | | | |
|---|---|---|---|
| 2,839,723 | 6/1958 | Armond | 324/65 P |
| 2,852,740 | 9/1958 | Posey et al. | 324/65 R |
| 3,181,058 | 4/1965 | Gulbrandsen | 324/65 R X |
| 3,242,473 | 3/1966 | Shivers, Jr. et al. | 324/65 R X |
| 3,427,537 | 2/1969 | Osborne | 324/65 R |

*Primary Examiner*—Stanley T. Krawczewicz
*Attorney, Agent, or Firm*—Richard W. Collins

[57] ABSTRACT

A portable apparatus for determining the moisture content in welding electrode coatings is described. The apparatus is suitable for field use, and comprises a source of low voltage direct current, a means for transforming low voltage direct current to high voltage direct current, an electrical circuit including a current indicating means and contacts attachable to a welding electrode whereby the welding electrode coating is included in the electrical circuit. A method of operating the apparatus to determine the amount of moisture in a welding electrode coating is also described.

3 Claims, 2 Drawing Figures

APPARATUS AND METHOD FOR DETERMINING MOISTURE CONTENT IN WELDING ELECTRODE COATINGS

BACKGROUND OF THE INVENTION

1. Field of the Invention

This invention relates to a method and apparatus for non-destructively measuring the moisture content in the inorganic coating of low hydrogen electric arc steel welding electrodes. More particularly, this invention relates to a low cost, light weight portable instrument suitable for field use, and to a method of using the instrument to determine the moisture content of welding electrodes.

A type of steel electric arc welding electrode commonly referred to as a "low hydrogen electrode" is used in some types of steel fabrication. For example, in the construction of off-shore well drilling and producing structures which are subject to heavy cyclical loadings, the use of these low hydrogen electrodes is often specified. Generally, the welds produced by these low hydrogen electrodes are less subject to hydrogen embrittlement. However, the inorganic coating portion of these low hydrogen electrodes must be free from moisture contamination in order to produce a sound weld. The maximum allowable moisture in the coating of a low hydrogen electrode is in the range of 0.02–0.5 percent by weight or in some cases even less.

2. Description of the Prior Art

The prevailing method of assuring that low hydrogen electrodes are sufficiently dry to be effective involves storing the electrodes in a sealed metal container until shortly before the electrodes are to be used. The containers in some cases are also stored in a heated environment to prevent accumulation of water. However, this method is not always successful as in some cases the containers develop leaks which enable an excessive amount of moisture to contaminate the normally hygroscopic inorganic coating of the welding electrodes. When the containers have once been opened, it is possible for moisture to accumulate rapidly on the unused welding electrodes in the container, as these welding electrodes are often used in areas having a high prevailing humidity, such as around shipyards.

There is no technique presently available for field use whereby the moisture content of a welding electrode can be accurately determined. The only methods previously avialable for determining moisture in welding electrode coatings involve laboratory procedures, such as set forth in American Welding Society Specification A.5.5–6.9; pages 25, 26 and 28. Alternative methods of welding electrode moisture measurement are discussed in "The Determination of Moisture in Electrode Coatings" by N. Jenkins and D. H. Parker — Welding Institute Bulletin, Volume 14, Number 10, pages 291 through 295. These methods are not adaptable to field use.

Portable moisture testing instruments for measuring the moisture content of certain materials such as cereal grains, paper, tobacco, wood and soil by conductivity measurement have been used in the past. However, these portable instruments for moisture determination have all been low voltage instruments which are only suitable for use in determining the moisture content of a material which contains a relatively high amount of moisture, such as from 5 to 30 percent or more. U.S. Pat. Nos. 2,466,453; 2,461,111 and 2,582,629 are exemplary of such low voltage instruments for determining the moisture content of materials. Prior to this invention, there has been no portable instrument suitable for field use which could accurately determine the moisture content of a non-conductive solid such as the inorganic coating of a low hydrogen electric arc welding electrode where the range of moisture content of interest is a fraction of one percent by weight. Such a device is provided by this invention.

SUMMARY OF THE INVENTION

According to the present invention, a portable instrument suitable for field use is provided. The instrument comprises a source of low voltage direct current, means for converting the low voltage direct current to a stable high voltage source, means for measuring current flow through the material to be tested, and means for attaching a welding electrode to the instrument such that the stable high voltage source can be applied across a portion of the inorganic coating of the welding electrode.

The method comprises providing a low voltage direct current source, transforming the low voltage direct current to a stable high voltage direct current source, providing a current measuring means, and determining the moisture content of a test specimen by reference to the current flowing through the test specimen when the stable high voltage source is applied thereto.

It is an object of this invention to provide a portable instrument suitable for field use which can determine the moisture level of the inorganic coating of a low hydrogen electric welding electrode wherein the moisture content is of the order of less than one percent by weight. It is a further object of the invention to provide a method for determining the moisture content of the coating of a low hydrogen electric welding electrode.

The above as well as additional objects and advantages are provided by this invention, as will be apparent from the following detailed description thereof.

DESCRIPTION OF THE PREFERRED EMBODIMENT

Figure 1:
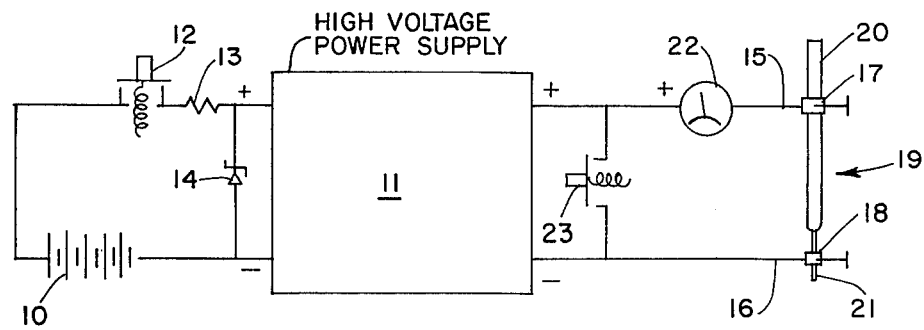
FIG. 1 is a schematic circuit diagram illustrating a moisture testing instrument in accordance with the invention.

The most preferred version of the invention will now be described by reference to the drawings.

A low voltage source 10, which may be a power cell having an output of from 6 to 15 volts, and which preferably is a small efficient battery such as a 12.6 volt nickel-cadmium battery, provides a source of low voltage direct current to a high voltage power supply 11. A normally open switch 12 activates the circuit, and a resistor 13 and a Zener diode 14 are utilized to regulate the low voltage supply to the high voltage power supply 11. The high voltage supply 11 transforms the low voltage direct current to a high voltage direct current having an electrical potential of from 600 to 1,500 volts. A preferred high voltage power supply is a unit identified as model K-15 available from the Venus Scientific Company of Farmingdale, N.Y. The Model K-15 high voltage power supply multiplies the input voltage by a factor by 100, and resistor 13 and diode 14 are preferably chosen to regulate the input to high voltage power supply 11 at about 10 volts such that the output from high voltage power supply 11 is about 1,000 volts. Two electrical leads 15 and 16 extend from high voltage power supply 11 to clamps or contact means 17 and 18 which are illustrated as clamps for attachment to a welding electrode 19. Contact means 17 is shown attached to the coating 20 of welding electrode 19, and contact means 18 is shown attached to the metal wire 21 of welding electrode 19. Alternatively, contact means 17 and 18 could both be attached to the coating 20 of electrode 19, in which case the resistance measured would be across the coating 20 at both contact points in series, whereas when contact means 18 is attached to the metal wire 21 of electrode 19, the resistance measured is only that across the coating at the point of contact means 17. A current measuring means 22 is provided on lead 15 for measuring the amount of current passing through the electrical circuit completed by attaching clamps 17 and 18 to welding electrode 19. The current measuring means 22 is preferably a micro ammeter calibrated to indicate a current from 0 to 100 micro amperes. A discharge switch 23 is provided across leads 15 and 16 for discharging the high voltage power supply means 11 after the measurement has been taken and the switch 12 has been opened. Discharge switch 23 enables the operator to dissipate any residual high voltage charge remaining after the normally open switch 12 is in the open position, such that the operator can remove the contact means 17 and 18 from welding electrode 19 without being subjected to the high voltage output of power supply 11.

An instrument as described above has several advantages over prior art portable moisture testing instruments. The instrument of this invention enables an operator to obtain a meaningful current reading across a test sample even though the test sample has a very high resistance, such as that of the inorganic coating of a low hydrogen electric welding electrode. The instrument can be calibrated such that the level of current indicated by current measuring means 22 is indicative of a particular moisture content in the test sample. A curve or curves of current versus moisture content can be developed by calibration of the instrument utilizing a series of welding electrodes of known moisture content.

Figure 2:
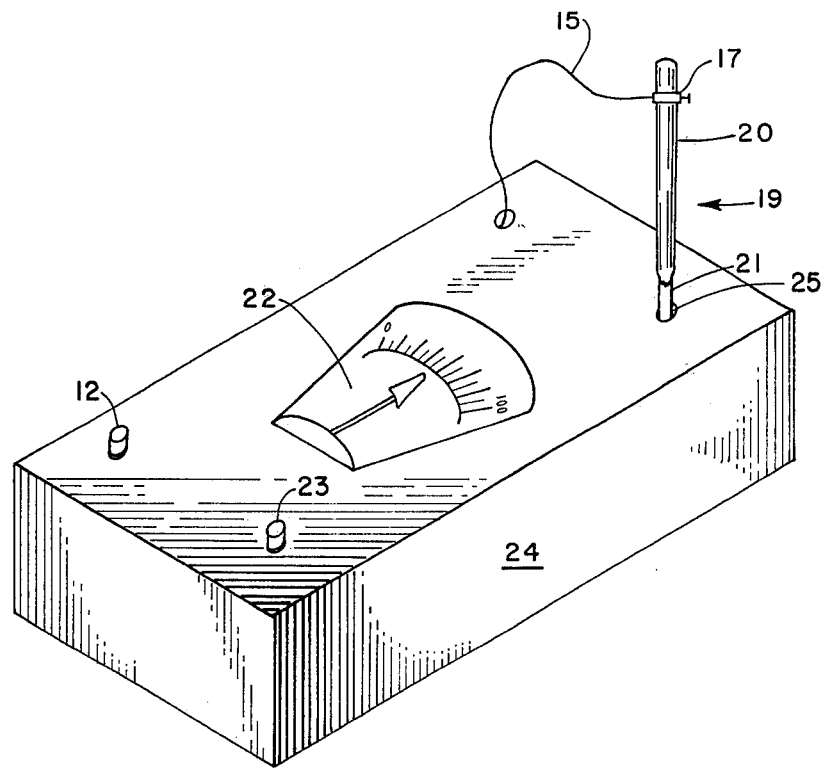
FIG. 2 is a perspective view of an instrument in accordance with the preferred embodiment of the invention.

A preferred instrument according to the invention is illustrated in FIG. 2. A housing 24 is shown with a charge switch 12 and a discharge switch 23 mounted thereon. A current measuring means 22 is also mounted on housing 24. The battery and high voltage power supply are enclosed within the housing. An electrical lead 15 and clamp 17 extend from housing 24, and clamp 17 is shown attached to the coating 20 of a welding electrode 19. The metal wire 21 of welding electrode 19 is shown inserted in a socket 25 in housing 24. Socket 25 is a friction contact means which takes the place of clamp 18 in FIG. 1. The circuitry from socket 25 to the high voltage power supply is enclosed within housing 24.

The method of this invention will be described as it would be carried out utilizing the instrument illustrated in FIG. 2. The metal wire 21 of welding electrode 19 is inserted in socket 25 in housing 24. Clamp 17 is attached to the coating 20 of rod 19, and charge switch 12 is closed to activate the circuit. The closing of charge switch 12 provides a regulated low voltage direct current source to the high voltage power supply, which provides a high voltage output across the welding electrode 19. The current indicated by current measuring means 22 is noted by the operator, and the moisture content of welding electrode 19 is then determined by reference to a calibration chart. After the current reading has been obtained, charge switch 12 is opened, and discharge switch 23 is closed to discharge the high voltage power supply. Clamp 17 is then removed from welding electrode 19 and the welding electrode is removed from socket 25, completing the test procedure. The tested welding electrode 19 is then either used or not used depending on the amount of moisture indicated by the test.

The instrument provided by this invention is portable, and can easily be constructed from components having a total weight of less than 1.5 kilograms. The high voltage power supply enables an operator to obtain a meaningful current reading even though the test specimen has a very high electrical resistance and a very low moisture content such as less than one percent. The instrument is quite rugged, and eminently suited for field use. The prior art methods for determining the moisture content of the inorganic coating of a welding electrode are not at all suitable for field use, and the previously available portable moisture testers were not suitable for measurement of a test specimen having a very high electrical resistance.

The foregoing description of the preferred embodiment of the apparatus and method of this invention is illustrative, and numerous variations and modifications of the embodiment described will be apparent to those skilled in the art. Such variations and modifications are to be considered a part of the invention, which is defined by the appended claims.

We claim:

1. A method for non-destructively determining the moisture content of the coating portion of a low hydrogen electric arc steel welding electrode having a non-conductive inorganic coating comprising:
   a. providing a low-voltage source of direct current;
   b. transforming the output of the low-voltage source of direct current to a high voltage direct current source;
   c. providing a circuit whereby said high voltage supplies electrical potential between two electrical contact means, said circuit including an electrical current indicating means for indicating the amount of electrical current flowing through said circuit;
   d. connecting one of said electrical contact means to said electrode;
   e. connecting the other of said electrical contact means to the inorganic coating portion of said electrode;
   f. completing said circuit whereby said high voltage is applied between said two electrical contact means; and
   g. determining the moisture content of said coating portion by reference to the output of said electrical current indicating means.

2. The method of claim 1 wherein said low voltage source provides an electrical potential of from 6 to 15 volts.

3. The method of claim 2 wherein said low voltage is transformed to a direct current source of from 600 to 1,500 volts.

* * * * *